United States Patent [19]

Lindgren

[11] Patent Number: 5,314,449
[45] Date of Patent: May 24, 1994

[54] RATE-ADAPTIVE CARDIAC PACEMAKER

[75] Inventor: Anders Lindgren, Taeby, Sweden

[73] Assignee: Siemens Aktiengesellschaft, Munich, Fed. Rep. of Germany

[21] Appl. No.: 18,525

[22] Filed: Feb. 17, 1993

[30] Foreign Application Priority Data

Feb. 26, 1992 [EP] European Pat. Off. ........ 92103277.7

[51] Int. Cl.⁵ .................................................. A61N 1/365
[52] U.S. Cl. .................................................. 607/24
[58] Field of Search ........................... 607/5, 17, 20, 24

[56] References Cited

U.S. PATENT DOCUMENTS

| | | |
|---|---|---|
| 4,462,406 | 7/1984 | DeCote, Jr. . |
| 4,702,253 | 10/1987 | Nappholz et al. . |
| 4,870,967 | 10/1989 | Heinze et al. ........................ 607/17 |
| 4,901,725 | 2/1990 | Nappholz et al. . |
| 5,036,849 | 8/1991 | Hauck et al. . |
| 5,058,583 | 10/1991 | Geddes et al. ..................... 607/624 |
| 5,074,304 | 12/1991 | Hedin et al. . |
| 5,154,171 | 10/1992 | Chirife ................................ 607/24 |
| 5,201,808 | 4/1993 | Steinhaus et al. ................... 607/20 |

FOREIGN PATENT DOCUMENTS 0308536 3/1989 European Pat. Off. .
2070282 9/1981 United Kingdom .

*Primary Examiner*—William E. Kamm
*Attorney, Agent, or Firm*—Hill, Steadman & Simpson

[57] ABSTRACT

A cardiac pacemaker, whose stimulation rate is controlled dependent on an impedance signal acquired between two electrodes, has one of the two electrodes disposed in an atrial electrode catheter and the other electrode being disposed in a separate, ventricular electrode catheter. Catheters carrying only a single electrode can thus be used, thereby avoiding the use of a bipolar electrode catheter. The two electrodes are respectively connected to two different stimulation pulse generators within the pacemaker housing, constructed as a dual chamber pacemaker.

5 Claims, 1 Drawing Sheet

RATE-ADAPTIVE CARDIAC PACEMAKER

BACKGROUND OF THE INVENTION

1. Field of the Invention

The present invention is directed to a rate-adaptive cardiac pacemaker for generating stimulation pulses at a rate correlated to the physical activity of the person in whom the pacemaker is implanted, of the type having an electrode arrangement with at least two electrodes disposed in the heart, and impedance measuring means for acquiring the electrical impedance between the two electrodes and a control means for controlling the pulse rate dependent on the acquired impedance signal.

2. Description of the Prior Art

A rate-adaptive cardiac pacemaker, wherein the stimulation pulse rate is controlled on the basis of an impedance measurement made between two electrodes disposed in the heart, is disclosed in European Application 0 327 292. The stimulation pulse generator and the impedance measuring means are both connected, through controllable switches, to two electrodes which are spaced from each other within an electrode catheter which is introduced into the heart of the patient. The impedance between the two electrodes, which changes dependent both on cardiac activity and on the respiration of the patient, is acquired by the impedance measuring means in the pauses between the stimulation pulses. The frequency components correlated with respiration are filtered out of the impedance signal, and the breadth-per-minute volume is identified therefrom, which is used for controlling the stimulation rate of the pulse generator.

In a similar cardiac pacemaker disclosed in U.S. Pat. No. 4,702,253, three electrodes are arranged within a single electrode catheter, with the stimulation pulses being generated between a first of these three electrodes and a reference electrode formed by the housing of the pacemaker, a constant test current for measuring impedance is generated between a second of the three electrodes and the reference electrode, and the voltage drop produced in the heart by the test current is measured as impedance signal between the third electrode and the reference electrode.

Both of these known cardiac pacemakers necessarily employ electrode catheters having two (bipolar) or more electrodes. In contrast to unipolar electrode catheters having only one electrode, such multiple electrode catheters are comparatively thick and inflexible.

SUMMARY OF THE INVENTION

It is an object of the present invention to provide a rate-adaptive cardiac pacemaker which undertakes an impedance measurement as the basis for controlling the stimulation pulse rate in a dual chamber cardiac pacemaker without the use of electrode catheters having multiple poles.

The above object is achieved in accordance with the principles of the present invention in a rate-adaptive pacemaker having impedance measuring means connected to two electrodes, one electrode being disposed in a first, atrial electrode catheter and the other electrode being disposed in a second, ventricular electrode catheter. The two electrodes are connected to two different stimulation pulse generators within cardiac pacemaker housing, which is constructed as a dual chamber pacemaker. Measurement of the impedance ensues using the two electrode catheters, which are already present in a conventional dual chamber pacemaker, so that no special or extra electrode catheter having two or more poles is necessary for the impedance measurement.

The aforementioned two known rate adaptive pacemakers are both single chamber pacemakers, are thus constructed only for the connection of a single electrode catheter. By contrast, in a dual chamber pacemaker, terminals for two electrode catheters are already provided, so that modification of the electrode connection configuration of a conventional dual chamber cardiac pacemaker is not required for achieving the impedance measurement of the invention. In accordance with the principles of the invention, means are provided within the pacemaker housing (which are not present in a conventional dual chamber pacemaker), for undertaking an impedance measurement employing the two-separately catheterized electrodes.

In one embodiment of the invention, the impedance measuring means includes a current or voltage source for generating a test current or a test voltage between an output terminal and a reference potential terminal formed by the housing of the pacemaker, and the atrial electrode, through a first, controllable switch arrangement, and the ventricular electrode, through a second, controllable switch arrangement, are selectively connectable to the output terminal or to the reference potential terminal. This permits the test current or the test voltage to be optionally generated between both electrodes or between one of the two electrodes and the pacemaker housing.

In another embodiment of the invention, the impedance measuring means includes a measuring amplifier having two input terminals, one input terminal being selectively connectable through a third, (i.e., different from the aforementioned first and second) controllable switch arrangement to the atrial electrode or to the ventricular electrode, and the other input terminal is selectively connectable through a fourth, controllable switch arrangement to one of the two electrodes or to the reference potential terminal. This permits the impedance signal to be selectively acquired between the two electrodes or between one of the two electrodes and the reference potential terminal.

DESCRIPTION OF THE PREFERRED EMBODIMENTS

Figure 1:
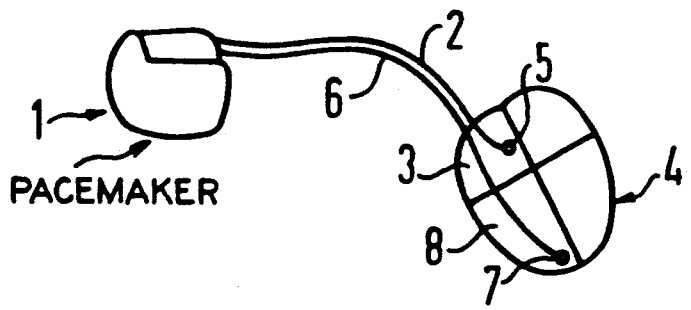
FIG. 1 is a schematic illustration showing a cardiac pacemaker constructed in accordance with the principles of the present invention as implanted in a patient, with electrodes leading to the patient's heart.

A cardiac pacemaker 1 in the form of a dual chamber cardiac pacemaker is shown in FIG. 1. The pacemaker 1 includes a first, atrial electrode catheter 2, which terminates in a first electrode 5 at its distal end, which is placed in the right atrium 3 of the heart 4 of a patient in whom the pacemaker 1 is implanted. The pacemaker 1 also includes a second, ventricular electrode catheter which terminates in a second electrode 7 at its distal end, which is introduced into the right ventricle 6 of the heart 4.

Figure 2:
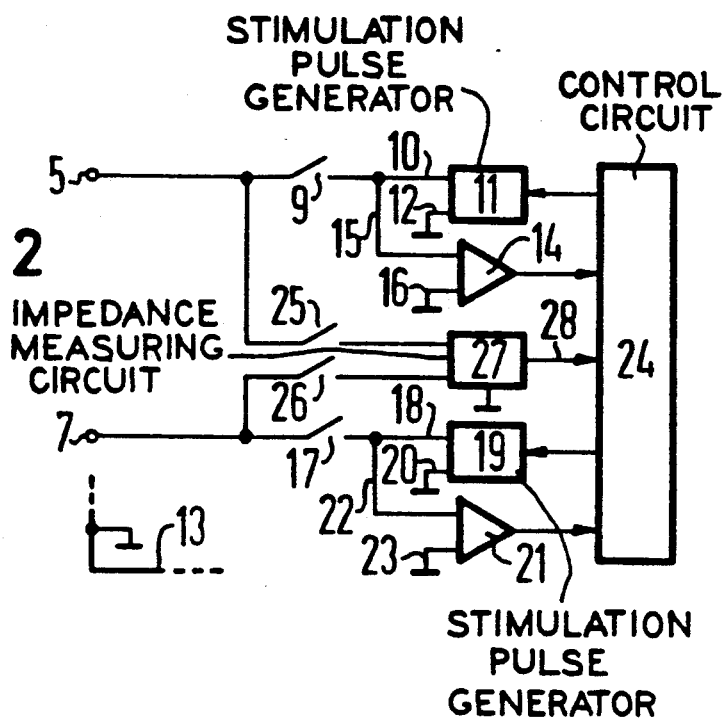
FIG. 2 is a schematic block diagram of the relevant circuitry for the cardiac pacemaker constructed in accordance with the principles of the present invention.

The details of the pacemaker constructed in accordance with the principles of the present invention are shown in block circuit form in FIG. 2. The atrial electrode 5 is connected to a first output terminal 10 of a stimulation pulse generator 11 through a controllable switch 9. The stimulation pulse generator 11 has a second output terminal 12 which is electrically connected to the housing 13 of the pacemaker 1, so that the second output terminal 12 and the housing 13 are at the same electrical potential. A detector 14 for detecting atrial events has a first input terminal 15 connected to the output terminal 10 of the stimulation pulse generator 11, and has a second input terminal 16 connected to the pacemaker housing 13.

The ventricular electrode 7 is connected through a second controllable switch 17 to an output terminal 18 of a second stimulation pulse generator 19. The second stimulation pulse generator 19 has a second output terminal 20 connected to the pacemaker housing 13. A further detector 21 for detecting ventricular events has a first input terminal 22 connected to the output terminal 18 of the second stimulation pulse generator 19, and has a second input terminal 23 connected to the pacemaker housing 13. The two stimulation pulse generators 11 and 19 and the two detectors 14 and 21 are connected to pacemaker control circuitry 24, which starts a base time interval after each stimulated event or detected natural event in the atrium 3, and initiates the output of a stimulation pulse in the atrium by the atrial stimulation pulse generator 11 if the base time interval expires without a natural atrial event having been detected by the atrial detector 11. After each stimulated or detected natural event in the atrium, an atrial-ventricular time interval is started, and the output of a stimulation pulse to the ventricle 8 is triggered if the atrial-ventricular time interval expires without a natural event in the ventricle 8 having been detected by the detector 21.

An impedance measuring circuit 27, for measuring the impedance of the body tissue between the electrodes 5 and 7, and possibly between one of those electrodes and the pacemaker housing 13, is also connected to the atrial electrode 5 and to the ventricular electrode 7 through two further switches 25 and 26. The measured impedance represents a physiological function parameter which changes dependent both on the respiration of the patient and on the cardiac activity of the patient. The impedance signal from the impedance measuring circuit 27 is supplied through an output line 28 to the pacemaker control circuitry 24, wherein the base time interval is modified, after filtering of the impedance signal, dependent on the respiration of the patient, for example the breadth-per-minute volume, or dependent on the cardiac activity, for example changes in the cardiac volume per unit of time.

Figure 3:
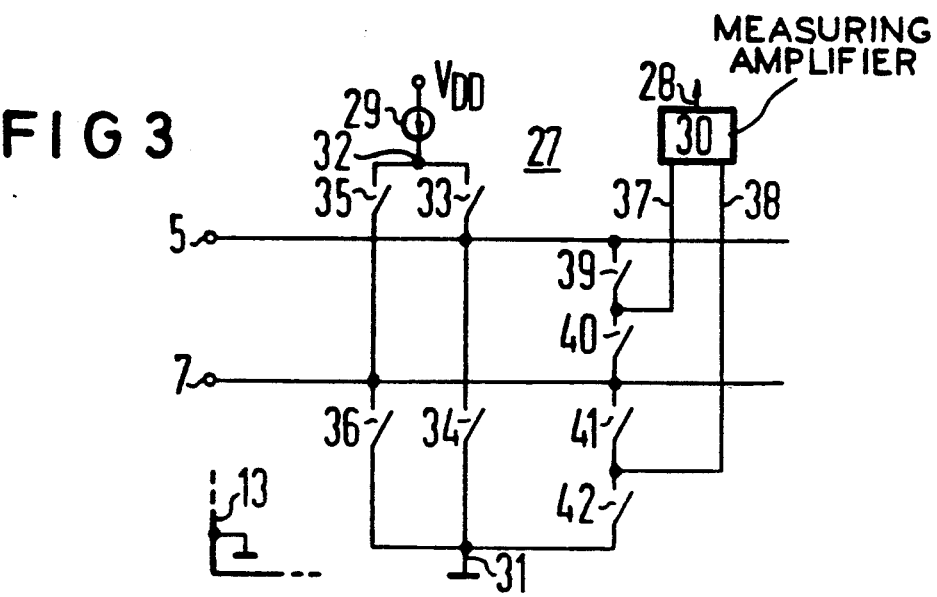
FIG. 3 is a schematic block diagram of an impedance measuring means for use in the cardiac pacemaker constructed in accordance with the principles of the present invention.

An exemplary embodiment of the impedance measuring circuit 27 is shown in FIG. 3, which includes a current source 29 and a measuring amplifier 30. The current source 29 is supplied by the supply voltage of a battery (not shown) of the pacemaker 1 tapped between a battery potential terminal $V_{DD}$ and a reference potential terminal 31 connected to the pacemaker housing 13. The current source 29 supplies an output in the form of current having a constant amplitude at its output terminal 32. As used herein, "constant amplitude" encompasses a pulsed current wherein the pulses are all of the same amplitude, and in fact the output of the current source 29 is preferably pulsed.

The atrial electrode 5 is connected to the output terminal 32 of the current source 29 and to the reference potential terminal 31 through a first, controllable switch arrangement composed of a switch 33 and a switch 34. Correspondingly, the ventricular electrodes 7 is connected to the output terminal 32 of the current source 29 and to the reference potential terminal 31 through a second, controllable switch arrangement composed of switches 35 and 36. Dependent on which of the switches 33 through 36 is closed, the current output from the current source 29 flows through the body impedance between the two electrodes 5 and 7, or between one of the two electrodes 5 or 7 and the pacemaker housing 13.

The measuring amplifier 30 has two input terminals 37 and 38; the input terminal 37 being selectively connectable to the atrial electrode 5 or to the ventricular electrode 7 through a third, controllable switch arrangement composed of the switches 39 and 40. The other input terminal 38 of the measuring amplifier 30 is selectively connectable to the ventricular electrode 7 or to the reference potential terminal 31 through a fourth, controllable switch arrangement composed of switches 41 and 42.

As an alternative to the specifically shown exemplary embodiment of FIG. 3, it is possible that the second input terminal 38 be connectable through the switch 41 to the atrial electrode 5, instead of to the ventricular electrode 7.

Dependent upon the respective states of the switches 39 through 42, the input side of the measuring amplifier 30 will be connected to the electrodes 5 and 7, or to one of the electrodes 5 and 7 and to the reference potential terminal 31. If all of the switches 33 through 36 and 39 through 42 are open, the current source 29 and the measuring amplifier 30 are uncoupled from the electrodes 5 and 7 and from the reference potential terminal 31, so that the stimulation pulse generators 11 and 19 and the detectors 14 and 21, and the measuring impedance circuit 27 cannot influence one another.

In particular, it should be noted that although the invention is illustrated in the exemplary embodiments as comprising an atrial electrode and a ventricular electrode carried on an atrial and a ventricular electrode catheter, respectively, it is also contemplated that the atrial and ventricular electrodes could be arranged on a common single catheter for inserting the atrial electrode in an atrial position and the ventricular electrode in a ventricular position.

Although modifications and changes may be suggested by those skilled in the art, it is the intention of the inventor to embody within the patent warranted hereon all changes and modifications as reasonably and properly come within the scope of his contribution to the art.

We claim as our invention:

1. A rate-adaptive implantable cardiac pacemaker comprising:
   implantable dual chamber pacing means including first stimulation pulse generating means for generating atrial stimulation pulses and second stimulation pulse generating means for generating ventricular stimulation pulses;
   a first electrode, electrically connected to said first stimulation pulse generating means, and arranged on a first electrode catheter adapted for inserting said first electrode in an atrial position of a heart to be stimulated;

a second electrode, electrically connected to said second stimulation pulse generating means, and arranged on said first or on a second electrode catheter adapted for inserting said second electrode in a ventricular position of said heart to be stimulated;

implantable impedance measuring means, electrically connected to said first and second electrodes, for acquiring a measurement of the electrical impedance between said first and second electrodes as an indicator of the level of physical activity of a patient in whom said pacemaker is implanted; and control means electrically connected to said impedance measuring means and to said first and second stimulation pulse generating means for causing said first and second stimulation pulse generating means to respectively generate stimulation pulses at a rate matched to said physical activity level of said patient.

2. A rate-adaptive cardiac pacemaker as claimed in claim 1 further comprising a power source and an implantable pacemaker housing containing said power source, said dual chamber pacing means, said impedance measuring means and said control means, and wherein said impedance measuring means comprises:

means, connected to said power source, for generating an electrical test signal between an output terminal of said means for generating a test signal and a reference potential terminal formed by said pacemaker housing;

first controllable switch means for selectively connecting said atrial electrode to said output terminal or to said reference potential terminal; and second controllable switch means for selectively connecting said ventricular electrode to said output terminal or to said reference potential terminal.

3. A rate-adaptive cardiac pacemaker as claimed in claim 2 wherein said impedance measuring means further comprises:

a measuring amplifier having two input terminals;

third controllable switch means for selectively connecting one of said input terminals of said measuring amplifier to said atrial electrode or to said ventricular electrode; and fourth controllable switch means for selectively connecting the other of said input terminals of said measuring amplifier to one of said atrial or ventricular electrodes or to said reference potential terminal.

4. A rate-adaptive cardiac pacemaker as claimed in claim 2 wherein said means for generating an electrical test signal is a voltage source for generating a test voltage across said output terminal and said reference potential terminal.

5. A rate-adaptive cardiac pacemaker as claimed in claim 2 wherein said means for generating an electrical test signal is a current source for generating a test current flowing between said output terminal and said reference potential terminal.

* * * * *